United States Patent [19]

Robertson et al.

[11] Patent Number: 5,225,431
[45] Date of Patent: Jul. 6, 1993

[54] THERAPEUTIC SUBSTITUTED INDOLE COMPOUNDS AND COMPOSITIONS THEREOF

[75] Inventors: Alan D. Robertson; Graeme R. Martin; Janet S. Buckingham, all of Beckenham, England

[73] Assignee: Burroughs Wellcome Co., Research Triangle Park, N.C.

[21] Appl. No.: 660,966

[22] Filed: Feb. 26, 1991

Related U.S. Application Data

[63] Continuation of Ser. No. 260,885, Oct. 21, 1988, abandoned.

[30] Foreign Application Priority Data

Oct. 23, 1987 [GB] United Kingdom ................. 8724912

[51] Int. Cl.$^5$ ................. A61K 31/415; C07D 403/06; C07D 403/04
[52] U.S. Cl. .................................... 514/389; 514/391; 548/312.1
[58] Field of Search ............................ 548/309, 312.1; 514/389, 391

[56] References Cited

U.S. PATENT DOCUMENTS

4,851,406 7/1989 Mertens et al. ..................... 514/389

FOREIGN PATENT DOCUMENTS

| | | |
|---|---|---|
| 81845/87 | 6/1988 | Australia . |
| 903778 | 12/1984 | Belgium . |
| 1165765 | 4/1984 | Canada . |
| 0145459 | 6/1985 | European Pat. Off. . |
| 0147107 | 7/1985 | European Pat. Off. . |
| 0162592 | 11/1985 | European Pat. Off. . |
| 0162593 | 11/1985 | European Pat. Off. . |
| 0191562 | 8/1986 | European Pat. Off. . |
| 0210840 | 2/1987 | European Pat. Off. . |
| 0219193 | 4/1987 | European Pat. Off. . |
| 0219929 | 4/1987 | European Pat. Off. . |
| 0221629 | 5/1987 | European Pat. Off. . |
| 0221725 | 5/1987 | European Pat. Off. . |
| 0224332 | 6/1987 | European Pat. Off. . |
| 0225726 | 6/1987 | European Pat. Off. . |
| 0237678 | 9/1987 | European Pat. Off. . |
| 0240096 | 10/1987 | European Pat. Off. . |
| 0242939 | 10/1987 | European Pat. Off. . |
| 0242973 | 10/1987 | European Pat. Off. . |
| 0244085 | 11/1987 | European Pat. Off. . |
| 0254433 | 1/1988 | European Pat. Off. . |
| 0266899 | 5/1988 | European Pat. Off. . |
| 0269452 | 6/1988 | European Pat. Off. . |
| 0276163 | 7/1988 | European Pat. Off. . |
| 2035310 | 6/1980 | United Kingdom . |
| 2081717 | 2/1982 | United Kingdom . |
| 2082175 | 3/1982 | United Kingdom . |
| 2083463 | 3/1982 | United Kingdom . |
| 2124210 | 2/1984 | United Kingdom . |
| 2129795 | 5/1984 | United Kingdom . |
| 2150932 | 7/1985 | United Kingdom . |
| 2153821 | 8/1985 | United Kingdom . |
| 2162522 | 2/1986 | United Kingdom . |
| 2168347 | 6/1986 | United Kingdom . |
| 2168973 | 7/1986 | United Kingdom . |
| 2175585 | 12/1986 | United Kingdom . |
| 2185020 | 7/1987 | United Kingdom . |
| 2186874 | 8/1987 | United Kingdom . |
| 2191488 | 12/1987 | United Kingdom . |
| 2192885 | 1/1988 | United Kingdom . |

OTHER PUBLICATIONS

Keery et al., *Brit. J. Pharm.*, vol. 89 (Supplement), p. 834p, (1986).
Finkbeiner, H., *J. Org. Chem.*, vol. 30(10), pp. 3414–3419 (1965).
A. Doenicke, et al., *The Lancet*, Jun. 11, 1988, pp. 1309–1311.
V. L. Perrin, *Clinical Pharmacokinetics* 10: pp. 334–352, (1985).

*Primary Examiner*—Mary C. Lee
*Assistant Examiner*—Lenora Miltenberger
*Attorney, Agent, or Firm*—Donald Brown; Lawrence A. Nielsen; Hannah O. Green

[57] ABSTRACT

The present invention is concerned with compounds of formula (I)

(Abstract continued on next page.)

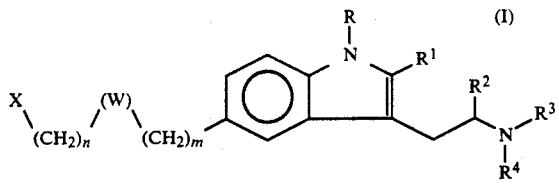

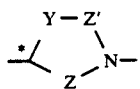

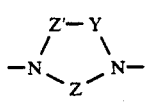

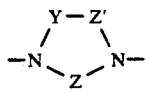

wherein
R, R¹ and R² are independently selected from hydrogen and $C_{1-4}$ alkyl;
R³ and R⁴ are independently selected from hydrogen, $C_{1-6}$ alkyl (including cycloalkyl) and aryl (wherein the alkyl or aryl group, which latter includes benzyl, is optionally substituted by one or more atoms or groups independently selected from halogen, $C_{1-4}$ alkyl and aryl), provided R³ benzyl or substituted benzyl when R⁴=H;
m is an integer of from 0 to 2;
n is an integer of from 0 to 3;
(W) is a group of formula (i), (ii), (iii), or (iv)

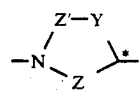

wherein Y is selected from oxygen, methylene and >N—R⁵, where R⁵ is hydrogen, $C_{1-4}$ alkyl, or benzyl, Z and Z' are independently selected from >C=O, >C=S and methylene, and the chiral center * in formula (i) or (ii) is in its (S) or (R) form or is a mixture thereof in any proportions;
X is a group selected from
aryl (including heteroaryl)
xanthenyl
dibenzofuranyl
which group is optionally substituted;

and salts and solvates thereof, the preparation of these compounds, pharmaceutical formulations containing them and their use in medicine, particularly in the treatment of migraine.

9 Claims, No Drawings

THERAPEUTIC SUBSTITUTED INDOLE COMPOUNDS AND COMPOSITIONS THEREOF

This is a continuation of copending application Ser. No. 07/260,885 filed on Oct. 21, 1988, now abandoned.

The present invention is concerned with new chemical compounds, their preparation, pharmaceutical formulations containing them and their use in medicine, particularly in the treatment of migraine.

Receptors which mediate the actions of 5-hydroxytryptamine (5-HT) have been identified in mammals in both the periphery and the brain. According to the classification and nomenclature proposed in a recent article (Bradley et al, Neuropharmac., 25, 563 (1986)), these receptors may be classified into three main types, viz. "5-HT$_1$-like", 5-HT$_2$ and 5-HT$_3$. Various classes of compounds have previously been proposed as 5-HT agonists or antagonists for therapeutic use, but these have not always been specific to a particular type of 5-HT receptor. We have now discovered a novel class of 5-HT agonists which are specific to a particular type of "5-HT$_1$-like" receptor and will be effective therapeutic agents for the treatment of clinical conditions in which a selective agonist for this type of receptor is indicated. For example, the receptor in question mediates vasoconstriction in the carotid vascular bed and thereby modifies blood flow therein; the compounds of the invention will therefore be beneficial in the treatment or prophylaxis of conditions wherein vasoconstriction in this bed is indicated, for example, migraine, a condition associated with excessive dilation of the carotid vasculature. However, it is within the scope of the present invention that the target tissue may be any tissue wherein action is mediated by "5-HT$_1$-like" receptors of the type referred to above.

According to a first aspect of the present invention, there is provided a compound of formula (I)

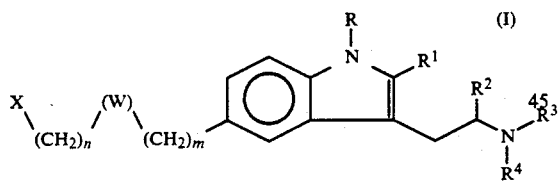

wherein

R, R$^1$ and R$^2$ are independently selected from hydrogen and C$_{1-4}$ alkyl;

R$^3$ and R$^4$ are independently selected from hydrogen, C$_{1-6}$ alkyl (including cycloalkyl) and aryl (wherein the alkyl or aryl group, which latter includes benzyl, is optionally substituted by one or more atoms or groups independently selected from halogen, C$_{1-4}$ alkyl and aryl), provided R$^3 \neq$ benzyl or substituted benzyl when R$^4$=H;

m is an integer of from 0 to 2;

n is an integer of from 0 to 3;

(W) is a group of formula (i), (ii), (iii), or (iv)

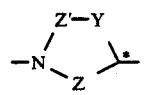 (i)

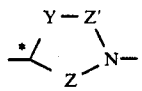 (ii)

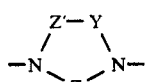 (iii)

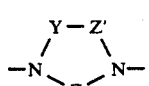 (iv)

wherein Y is selected from oxygen, methylene and >N—R$^5$, where R$^5$ is hydrogen, C$_{1-4}$ alkyl, or benzyl, Z and Z' are independently selected from >C=O, >C=S and methylene, and the chiral centre * in formula (i) or (ii) is in its (S) or (R) form or is a mixture thereof in any proportions;

X is a group selected from
aryl (including heteroaryl)
xanthenyl
dibenzofuranyl
which group is optionally substituted by an atom or group selected from
C$_{1-6}$ alkyl (including cycloalkyl)
aryl (including heteroaryl)
C$_{1-4}$ alkoxy
aryloxy
alkylsulphonyl
arylsulphonyl
halogen
cyano
carbamoyl
alkylcarbamoyl
dialkylcarbamoyl
arylcarbamoyl
diarylcarbamoyl
carbamoylmethyl
N-alkylcarbamoylmethyl
N,N-dialkylcarbamoylmethyl
N-arylcarbamoylmethyl
N,N-diarylcarbamoylmethyl
alkoylamino
aroylamino
alkoylaminomethyl
aroylaminomethyl
alkylsulphamino
arylsulphamino
alkylsulphaminomethyl
arylsulphaminomethyl
sulphamyl
alkylsulphamyl
dialkylsulphamyl
arylsulphamyl
diarylsulphamyl
the aryl group(s) of aryl-containing substituents being optionally substituted by halogen or C$_{1-4}$ alkoxy;
and physiologically acceptable salts and solvates thereof.

Compounds of formula (I) having particularly desirable pharmacological properties for the treatment or prophylaxis of migraine include those in which (W) is (i) wherein Y=O, CH$_2$, or NR$^5$, Z=CO or CH$_2$ and Z'=CO, (W) is (ii) wherein Y=CH$_2$ or NR$^5$ and Z=Z'=CO, (W) is (iii) wherein Y=CH$_2$ or NR$^5$, Z=CO and Z'=CO or CH$_2$, or (W) is (iv) wherein Y=CH$_2$, Z=CO and Z'=CO or CH$_2$, and X is a phenyl ring substituted by an alkylcarbamoyl, alkoylamino, or alkylsulphamino group.

Particularly preferred compounds of formula (I) include 2-{5-[1-(3-methylaminocarbonylbenzyl)-2,5-dioxoimidazolidin-4-ylmethyl]-1H-indol-3-yl}ethylamine, N,N-dimethyl-2-[5-{1-[2-(4-acetylaminophenyl)ethyl]-2,5-dioxoimidazolidin-4-ylmethyl}-1H-indol-3-yl]ethylamine, N-methyl-2-{5-[1-(3-methylaminocarbonylbenzyl)-2,5-dioxoimidazolidin-4-ylmethyl]-1H-indol-3-yl}ethylamine, 2-{5-[1-(3-acetylaminobenzyl)-2,5-dioxoimidazolidin-4-ylmethyl]-1H-indol-3-yl}ethylamine and 2-{5-[1-(3-methylsulphonylaminobenzyl)-2,5-dioxoimidazolidin-4-ylmethyl]-1H-indol-3-yl}ethylamine; in particular, salts thereof.

Physiologically acceptable salts of the present compounds are particularly suitable for medical purposes because of their greater aqueous solubility relative to the parent, i.e. basic, compounds. Such salts must clearly have a physiologically acceptable anion. Suitable physiologically acceptable salts include those derived from acetic, hydrochloric, hydrobromic, phosphoric, malic, maleic, fumaric, citric, sulphuric, lactic, or tartaric acid. The maleate and chloride salts are particularly preferred for medical purposes. Salts having a non-physiologically acceptable anion are within the scope of the invention as useful intermediates for the preparation of physiologically acceptable salts and/or for use in non-therapeutic, for example, in vitro, situations.

According to a second aspect of the present invention, there is provided a compound of formula (I) or a physiologically acceptable salt or solvate thereof for use as a selective "5-HT$_1$-like" receptor agonist, for example, as a vasoconstrictor, in a method of treatment of the human or animal body by therapy, such as the treatment or prophylaxis of migraine. As indicated earlier, however, target organs for the present compounds other than the carotid vasculature are within the scope of the present invention.

The amount of a compound of formula (I), or a salt or solvate thereof, which is required to achieve the desired biological effect will depend on a number of factors such as the specific compound, the use for which it is intended, the means of administration, and the recipient. A typical daily dose for the treatment of migraine may be expected to lie in the range 0.05 to 30 mg per kilogram body weight. Unit doses may contain from 1 to 500 mg of a compound of formula (I), for example, ampoules for injection may contain from 1 to 50 mg and orally administrable unit dose formulations such as tablets or capsules may contain from 1 to 500 mg. Such unit doses may be administered one or more times a day, separately or in multiples thereof. An intravenous dose may be expected to lie in the range 0.05 to 50 mg/kg and would typically be administered as an infusion of from 0.0005 to 2.0 mg per kilogram per minute. Infusion solutions suitable for this purpose may contain from 0.01 to 10 mg/ml.

When the active compound is a salt or solvate of a compound of formula (I), the dose is based on the cation (for salts) or the unsolvated compound.

Hereinafter references to "compound(s) of formula (I)" will be understood to include physiologically acceptable salts and solvates thereof.

According to a third aspect of the present invention, therefore, there are provided pharmaceutical compositions comprising, as active ingredient, at least one compound of formula (I) and/or a pharmacologically acceptable salt or solvate thereof together with at least one pharmaceutical carrier or excipient. These pharmaceutical compositions may be used in the treatment or prophylaxis of clinical conditions for which a selective "5-HT$_1$-like" receptor agonist of the present type is indicated, e.g. migraine. The carrier must be pharmaceutically acceptable to the recipient and must be compatible with, i.e. not have a deleterious effect upon, the other ingredients in the composition. The carrier may be a solid or liquid and is preferably formulated with at least one compound of formula (I) as a unit dose formulation, for example, a tablet which may contain from 0.05 to 95% by weight of the active ingredient. If desired, other pharmacologically active ingredients may also be incorporated in the pharmaceutical compositions of the invention.

Possible formulations include those suitable for oral, rectal, topical (for example, buccal, such as sub-lingual), or parenteral (for example, subcutaneous, intramuscular, or intravenous) administration. The most suitable means of administration for a particular patient will depend on the nature and severity of the condition being treated and on the nature of the active compound, but, where possible, oral administration is preferred.

Formulations suitable for oral administration may be provided as discrete units, such as tablets, capsules, cachets, or lozenges, each containing a predetermined amount of the active compound; as powders or granules; as solutions or suspensions in aqueous or non-aqueous liquids; or as oil-in-water or water-in-oil emulsions.

Formulations suitable for buccal administration include lozenges comprising the active compound and, typically, a flavoured base, such as sugar and acacia or tragacanth, and pastilles comprising the active compound in an inert base, such as gelatin and glycerin or sucrose and acacia.

Formulations suitable for parenteral administration typically comprise sterile aqueous solutions containing a predetermined concentration of the active compound; the solution is preferably isotonic with the blood of the intended recipient. Although such solutions are preferably administered intravenously, they may also be administered by subcutaneous or intramuscular injection.

Formulations suitable for rectal administration are preferably provided as unit-dose suppositories comprising the active ingredient and one or more solid carriers forming the suppository base, for example, cocoa butter.

Formulations suitable for topical application include ointments, creams, lotions, pastes, gels, sprays, aerosols and oils. Suitable carriers for such formulations include petroleum jelly, lanolin, polyethylene glycols, alcohols, and combinations thereof. The active ingredient is typically present in such formulations at a concentration of from 0.1 to 15% w/w.

The formulations of the invention may be prepared by any suitable method, typically by uniformly and intimately admixing the active compound(s) with liquids or finely divided solid carriers, or both, in the required proportions and then, if necessary, shaping the resulting mixture into the desired shape.

For example, a tablet may be prepared by compressing an intimate mixture comprising a powder or granules of the active ingredient and one or more optional ingredients, such as a binder, lubricant, inert diluent, or surface active dispersing agent, or by moulding an intimate mixture of powdered active ingredient and inert liquid diluent.

Aqueous solutions for parenteral administration are typically prepared by dissolving the active compound in sufficient water to give the desired concentration and then rendering the resulting solution sterile and isotonic.

Thus, according to a fourth aspect of the present invention, there is provided the use of a compound of formula (I) in the preparation of a pharmaceutical formulation for the treatment or prophylaxis of clinical conditions in which a selective agonist for the particular type of "5-HT$_1$-like" receptor described herein is indicated, for example, migraine.

According to a fifth aspect, there is provided a method of treating or preventing clinical conditions in which a selective agonist for the particular type of "5-HT$_1$-like" receptor described herein is indicated, for example, migraine, using a compound of formula (I) or a pharmaceutical formulation containing such a compound.

According to a sixth aspect of the invention, compounds of formula (I) may be prepared by any suitable process, for example, by reacting a compound of formula (II)

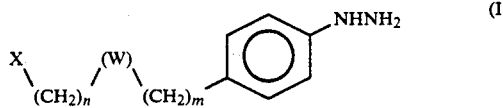

wherein n, m, (W) and X are as hereinbefore defined, with a compound of formula (III)

or a carbonyl-protected form thereof, such as the dimethyl acetal, wherein $R^1$ is as hereinbefore defined and Y is either —CH($R^2$)L wherein $R^2$ is as hereinbefore defined and L is (a) a suitable leaving group, such as chloro, and the initial product is aminated, (b) a protected form of amino group, for example, phthalimido, and the initial product is deprotected, (c) a nitro group and the initial product is reduced, or (d) a group —NR$^3$R$^4$ wherein R$^3$ and R$^4$ are as hereinbefore defined other than hydrogen, or Y is cyano and the initial product is reduced. Methods by which the initial products may be aminated, deprotected, or reduced are well known to those skilled in the art.

The reaction of compounds (II) and (III) to give a compound of formula (I) may be carried out in a single step (Fischer indole synthesis) or by an initial non-cyclising step at a lower temperature to give a compound of formula

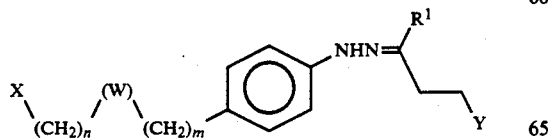

wherein $R^1$, (W), X, Y, m and n are as hereinbefore defined, followed by cyclisation using a suitable reagent, such as a polyphosphate ester, to give a compound of formula (I).

Standard N-alkylation/arylation methods may be used to convert compounds of formula (I) wherein R, $R^3$ and/or $R^4$ are hydrogen to corresponding compounds wherein R, $R^3$ and/or $R^4$ are alkyl or aryl as hereinbefore defined.

Compounds of formula (I) wherein R=C$_{1-4}$ alkyl may be prepared from the corresponding compound wherein R=H by treatment with a suitable alkylating agent, such as methyl iodide, typically under basic conditions, for example, NaH/DMF.

Compounds of formula (I) wherein $R^3=R^4=C_{1-6}$ alkyl or aryl may be prepared from the corresponding compound wherein $R^3=R^4=H$ by methods of N-alkylation or N-arylation well known to those skilled in the art, for example, by treatment with the appropriate aldehyde in the presence of a reducing agent, for example, sodium cyanoborohydride.

Compounds of formula (I) wherein $R^3$ or $R^4=C_{1-6}$ alkyl or aryl may be prepared from the corresponding compound wherein $R^3=R^4=H$ by N-benzylation using benzaldehyde and a suitable reducing agent, for example, sodium borohydride, followed by N-alkylation or N-arylation using a suitable agent, such as dimethyl sulphate, typically under basic conditions, for example, anhy. K$_2$CO$_3$/DMF, and finally debenzylation by catalytic hydrogenation.

Hydrazines of formula (II) may be prepared from the corresponding anilines of formula (IV)

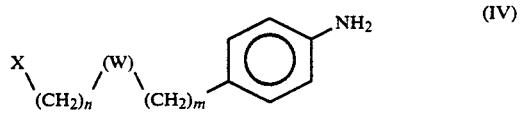

wherein m, n, p, (W) and X are as hereinbefore defined, by diazotisation followed by reduction. Diazotisation is typically carried out using sodium nitrite/c.HCl and the resulting diazo product reduced in situ using, for example, tin(II) chloride/c.HCl.

Anilines of formula (IV) may be prepared by reduction of the corresponding nitro compounds of formula (V)

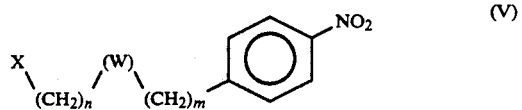

wherein m, n, p, (W) and X are as hereinbefore defined, typically by catalytic hydrogenation or using tin(II) chloride.

Nitro compounds of formula (V) may be prepared by (a) reacting a compound of formula (VI)

$$\text{(W}^1\text{)}\diagdown_{(CH_2)_m}\diagup\hspace{-2pt}\bigcirc\hspace{-2pt}\diagup^{NO_2} \quad \text{(VI)}$$

wherein m is as hereinbefore defined and (W$^1$) is

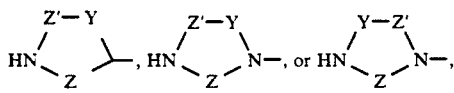

wherein Y, Z and Z' are as hereinbefore defined, with a compound of formula (VII)

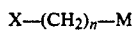 (VII)

wherein n and X are as hereinbefore defined and M is a suitable leaving group, such as chloro, bromo, or hydroxy, typically under basic conditions, for example, anhy. K$_2$CO$_3$/DMF or P-TBD/DCM (M=chloro or bromo) or DEAD/Ph$_3$P/DME (M=hydroxy). The latter conditions are suitable for the preparation of compounds of formula (V) wherein (W) is

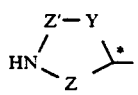

where * is a chiral centre.

Alternatively, a compound of formula (VI) wherein m is as hereinbefore defined and (W$^1$) is

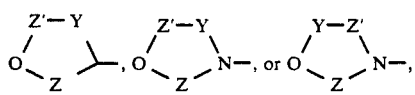

wherein Y, Z and Z' are as hereinbefore defined, may be reacted with a compound of formula (VII) wherein n and X are as hereinbefore defined and M is amino, typically in an aprotic solvent, followed by treatment with, for example, acetyl chloride;

(b) reacting a compound of formula (VIII)

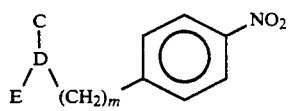 (VIII)

wherein m is as hereinbefore defined, D=CH or N, and C and E are as defined below, with a compound of formula (IX)

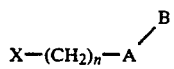 (IX)

wherein n and X are as hereinbefore defined and A and B are atoms or groups capable of reacting with groups E and C respectively to form a heterocyclic group

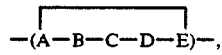, or reacting a compound of formula (VIIIA)

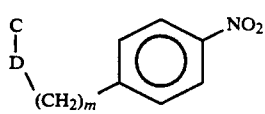 (VIIIA)

wherein m is as hereinbefore defined and C and D are as defined below, with a compound of formula (IXA)

 (IXA)

wherein n is as hereinbefore defined, A=CH or N, and B and E are groups capable of reacting with atoms or groups C and D to form a heterocyclic group

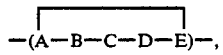, thereby forming a compound of formula (V)'

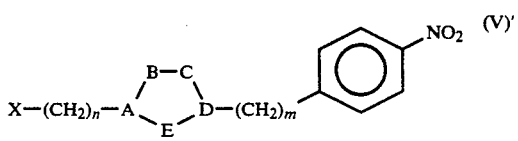 (V)' wherein m, n and X are as hereinbefore defined and

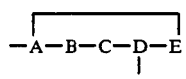

is the same as (W) in compounds of formula (V). For the preparation from (VIII) and (IX) of compounds of formula (V) wherein A=N, B=CO, C=O or NH, and E=CO, —A—B is typically —N=C=O, C is hydroxy or amino, and E is carboxy or carboalkoxy; for the preparation from (VIIIA) and (IXA) of compounds of formula (V) wherein B=O or NH, C=CO, D=N, and E=CO, —D—C is typically —N=C=O, B is hydroxy or amino, and E is carboxy or carboalkoxy.

(c) reacting a compound of formula (X)

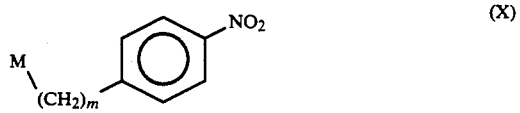 (X)

wherein m is as hereinbefore defined and M is a suitable leaving group, such as chloro, bromo, or hydroxy, with a compound of formula (XI)

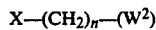 (XI)

wherein n and X are as hereinbefore defined and (W$^2$) is

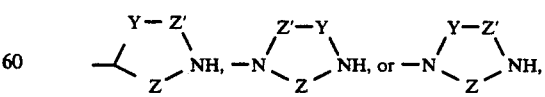

wherein Y, Z and Z' are as hereinbefore defined, typically under basic conditions, for example, anhy. K$_2$CO$_3$/DMF or P-TBD/DCM (M=chloro or bromo) or DEAD/Ph$_3$P/DME (M=hydroxy). The latter conditions are suitable for the preparation of compounds of formula (V) wherein (W$^2$) is

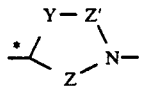

where * is a chiral centre.

Alternatively, a compound of formula (X) wherein m is as hereinbefore defined and M is amino, may be reacted with a compound of formula (XI) wherein n and X are as hereinbefore defined and (W²) is

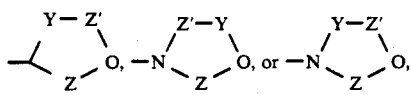

wherein Y, Z and Z' are as hereinbefore defined, typically in a aprotic solvent, followed by treatment with, for example, acetyl chloride; or (d) cyclising a compound of formula (XII)

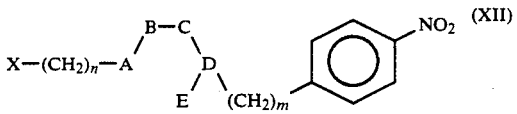

or (XIIA)

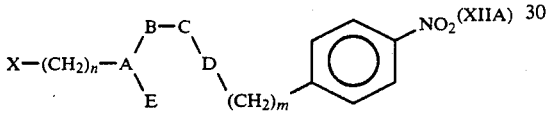

wherein m, n, A, B, C, D, E and X are as hereinbefore defined, typically in the presence of acid, to form a compound of formula (V)' wherein m, n and X are as hereinbefore defined and

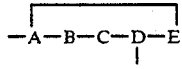

is the same as (W) in compounds of formula (V). This method is suitable for the preparation of compounds of formula (V) wherein (W) is

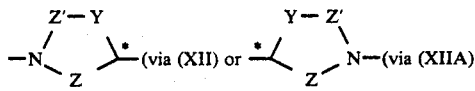

wherein * is a chiral centre. For the preparation of compounds of formula (V) wherein A=N, B=CO, C=NR⁵, where R⁵ is as hereinbefore defined, and E=CO, —A—B—C in compound (XII) or —B—C—D— in compound (XIIA) is typically —N-H—CO—NH— and E is carboxy or carboalkoxy.

Compounds of formula (V) wherein Y=NH may be converted to compounds of formula (V) wherein Y=NR⁵, where R⁵ is as hereinbefore defined other than hydrogen, by treatment with a suitable alkylating or arylating agent, such as methyl iodide, typically under basic conditions, for example, anhy. K₂CO₃/DMF.

Compounds of formula (V) wherein Z and/or Z'=CO may be converted to compounds of formula (IV) wherein Z and/or Z'=CH₂ by suitable reduction.

for example, when the carbonyl(s) is adjacent to a carbon atom, using sodium borohydride or lithium aluminum hydride (LAH) to form the alkene which is then catalytically hydrogenated. The latter step conveniently converts the nitro group of compound (V) to an amino group so that a separate reductive step is not required to prepare the aniline (IV).

Compounds of formula (VI) may be prepared by reacting a compound of formula (XIII)

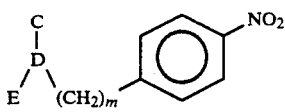

wherein m, C, D and E are as hereinbefore defined, with a compound or anion of formula A—B wherein A and B are as hereinbefore defined, to form a compound of formula (VI)'

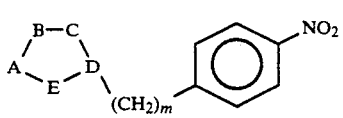

wherein m is as hereinbefore defined and

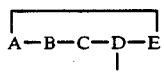

is the same as (W¹) is compounds of formula (VI). For the preparation of compounds of formula (VI) wherein A=NH, B=CO, C=NH and E=CO, A—B is typically cyanate anion, C is amino and E is carboxy or carboalkoxy. The reaction is carried out in a polar solvent and the resulting salt acidified in situ. This method is suitable for the preparation of compounds of formula (VI) wherein (W¹) is

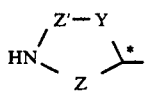

where * is a chiral centre.

Compounds of formula (VI) may also be prepared by reacting a compound of formula (X) as hereinbefore defined with a compound of formula H(W²) wherein (W²) is as hereinbefore defined, typically in the presence of base, for example, sodium hydroxide.

Compounds of formula (XI) may be prepared by reacting a compound of formula (IXA) wherein n, A, B, E and X are as hereinbefore defined, with a compound or anion of formula C—D wherein C and D are as hereinbefore defined, to form a compound of formula (XI)'

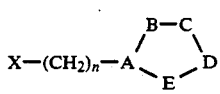

wherein n and X are as hereinbefore defined and

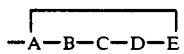

is the same as (W²) in compounds of formula (XI). For the preparation of compounds of formula (XI) wherein B=NH, C=CO, D=NH and E=CO, C—D is typically cyanate anion, B is amino and E is carboxy or carboalkoxy. The reaction is carried out in a polar solvent and the resulting salt acidified in situ.

Compounds of formulae (VI)' and (XI)' wherein, in (W¹) and (W²), B=E=CO, A=O and C=E=CO, D=O respectively, may be prepared by cyclisation of the appropriate dicarboxylic acid (XIV), for example, by treatment with acetyl chloride.

Compounds of formula (XII) may be prepared by reacting a compound of formula (XV)

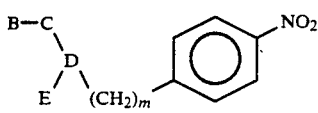
(XV)

wherein m, B, C, D and E are as hereinbefore defined, with a compound of formula (XVI)

(XVI)

wherein n and X are as hereinbefore defined and A is amino, typically in an aprotic solvent.

Compounds of formula (XIIA) may be prepared by reacting a compound of formula (XVII)

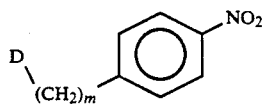
(XVII)

wherein m is as hereinbefore defined and D is amino, with a compound of formula (XVIII)

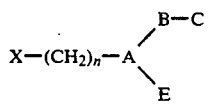
(XVIII)

wherein n, A, B, C, E and X are as hereinbefore defined, typically in an aprotic solvent.

Compounds of formula (VII), (VIII), (VIIIA), (IX), (IXA), (X), (XIII), (XIV), (XV), (XVI), (XVII) and (XVIII) can be obtained commercially or may be prepared from readily available starting materials by methods known to those skilled in the art or obtainable from the chemical literature.

For a better understanding of the invention, the following Examples are given by way of illustration.

Synthetic Examples 1 to 12 are concerned with the preparation of compounds of formula (V) which may be converted to compounds of formula (I) by steps analogous to those described in Synthetic Examples 13 to 16. All intermediates in the Synthetic Examples which have a chiral centre are racemic unless otherwise indicated. All flash chromatography described in the Synthetic Examples was carried out using Merck Kieselguhr 60 (230-400 mesh ASTM).

SYNTHETIC EXAMPLE 1

Preparation of N-Methyl-3-[4-(4-nitrobenzyl)-2,5-dioxoimidazolidinylmethyl]benzamide

(a) 4-(4-Nitrobenzyl)imidazolidin-2,5-dione

A solution of p-nitrophenylalanine (4.2 g, Fluka) and potassium cyanate (1.62 g) in water (6 ml) was refluxed for 1 hour. C.HCl (3 ml) was added and the mixture refluxed for a further 10 minutes, then cooled, diluted with water and filtered. The residue was washed with water and dried to give the desired product as a straw-coloured solid (3.85 g). The 200 MHz ¹H NMR was consistent with the proposed structure.

A sample was crystallised from ethanol to give pale cream needles, mp >235° C.

(b) 3-Chloromethyl-N-methylbenzamide

A solution of 3-chloromethylbenzoyl chloride (7.4 g, Aldrich) in DCM (35 ml) was added dropwise at 0° C. over 30 minutes to a stirred mixture of 30% aqu. methylamine (4.5 ml) and triethylamine (3.6 g) in DCM (50 ml). When addition was complete, the mixture was allowed to warm to room temperature over 1 hour with stirring. Further methylamine (0.5 ml) was added and the mixture stirred for a further 10 minutes, then washed with water, 1N aqu. HCl, 1N aqu. NaOH and brine, dried over MgSO₄ and evaporated in vacuo to give the desired product as a colourless oil which solidified to a white solid on standing.

(c) N-Methyl-3-[4-(4-nitrobenzyl)-2,5-dioxoimidazolidinylmethyl]benzamide

The product from step (a) (4.0 g), the product from step (b) (3.3 g) and anhy. K₂CO₃ (2.55 g) were taken up in DMF (25 ml) and stirred at room temperature for 60 hours. The mixture was poured with vigorous stirring into ice-water (175 ml) to give an oily precipitate. Ethyl acetate was added and stirring continued for 1 hour to solidify the precipitate. The latter was filtered off, washed with water, ethyl acetate and ether, and dried to give the desired product as a peach-coloured solid (4.5 g).

SYNTHETIC EXAMPLE 2

Preparation of (−)-4'-{2-[4-(4-Nitrobenzyl)-2,5-dioxoimidazolidinyl]ethyl}acetanilide

(a) (−)-4-(4-Nitrobenzyl)imidazolidin-2,5-dione

By the method of Synthetic Example 1, step (a), using p-nitro-L-phenylalanine (Fluka). $[\alpha]_D^{25}$ −88.2° (c=0.50, MeOH).

(b) 2-(4-Acetamidophenyl)ethyl acetate

A solution of acetyl chloride (35.6 ml) in dioxan (110 ml) was added dropwise at 0° C. to a stirred mixture of p-aminophenethyl alcohol (34.3 g, Aldrich) and triethylamine (37.5 g) in dioxan (110 ml). When addition was complete, the mixture was stirred at room temperature for 17 hours, then poured into 2N aqu. HCl, saturated with NaCl, and extracted with ethyl acetate (×3). The combined extracts were washed with water and brine, dried over MgSO₄ and evaporated in vacuo to give the desired product as a brown solid (55.3 g).

(c) 4'-(2-Hydroxyethyl)acetanilide

A solution of the product from step (b) (55.3 g) in methanol (250 ml) and 1N aqu. NaOH (500 ml) was stirred at room temperature for 1 hour. The methanol was evaporated in vacuo and the remaining aqueous solution adjusted to pH 4 (2N aqu. HCl), saturated with NaCl, and extracted with ethyl acetate ($\times$3). The combined extracts were washed with water and brine, dried over MgSO$_4$ and evaporated in vacuo to give a brown oil which was flash chromatographed through a silica column using ethyl acetate and then crystallised from ethyl acetate to give the desired product (51.7 g).

(d) (−)-4'-{2-[4-(4-Nitrobenzyl)-2,5-dioxoimidazolidinyl]ethyl}acetanilide

A solution of diethylazodicarboxylate (7.8 g) in DME (40 ml) was added dropwise under N$_2$ to a stirred mixture of the product from step (a) (10.5 g), the product from step (c) (8.0 g) and triphenylphosphine (11.7 g) in DME (400 ml). When addition was complete, the mixture was stirred at room temperature for 17 hours, then evaporated in vacuo and the residue crystallised from ethanol/ether (1:4 v/v) to give the desired product as a pale yellow solid (12.7 g), $[\alpha]_D^{25}$ −97.8° (c=0.50, MeOH).

SYNTHETIC EXAMPLE 3

Preparation of 1-Benzyl-3-(4-nitrobenzyl)imidazolidin-2,4-dione

(a) 3-(4-Nitrobenzyl)imidazolidin-2,4-dione

A solution of hydantoin (5.0 g, Aldrich) in 2N aqu. NaOH (25 ml) was stirred at room temperature for 1 hour, then a solution of p-nitrobenzyl bromide (10.8 g, Aldrich) in methanol (50 ml) was added and the mixture refluxed for 16 hours. The mixture was cooled and the pale yellow precipitate filtered off, dried in vacuo, and recrystalised from ethanol to give the desired product as pale yellow crystals (6.8 g).

(b) 1-Benzyl-3-(4-nitrobenzyl)imidazolidin-2,4-dione

A solution of the product from step (a) (5.9 g) in DMF (15 ml) was added under N$_2$ to a stirred suspension of anhy. K$_2$CO$_3$ (3.5 g) in DMF (15 ml), followed by the addition of benzyl bromide (4.3 g, Aldrich). After additions were complete, the mixture was stirred at room temperature for 16 hours, then poured into ice-water and extracted with ethyl acetate ($\times$3). The combined extracts were washed with brine, dried over MgSO$_4$ and evaporated to give a yellow oil which was flash chromatographed through a silica column using ethyl acetate to give the desired product as a yellow oil (7.0 g).

SYNTHETIC EXAMPLE 4

Preparation of 1-Benzyl-3-(4-nitrobenzyl)pyrrolidin-2,5-dione

A solution of benzylamine (1.2 g, Aldrich) in DCM (10 ml) was added dropwise over 5 minutes to a stirred suspension of p-nitrobenzylsuccinic anhydride (2.4 g, JCS Perkin I, 1975, 830) in DCM (10 ml). After initial exothermicity, mixture stirred at room temperature for 3 hours, then evaporated in vacuo to give a colourless foam to which benzene (20 ml) and acetyl chloride (5 ml) were added. The mixture was stirred for 20 minutes at room temperature, then refluxed for 5 hours. The acetyl chloride was distilled off to leave 10 ml of reaction mixture from which crystalline solid deposited on cooling. The solid was filtered off and washed with benzene to give the desired product as a very pale yellow solid (2.1 g), mp 135°-137° C. The 200 MHz $^1$H NMR was consistent with the proposed structure.

SYNTHETIC EXAMPLE 5

Preparation of 3-Benzyl-5-(4-nitrobenzyl)oxazolidin-2,4-dione

(a) 2-Hydroxy-3-(4-nitrophenyl)propionic acid

A solution of sodium nitrite (4.6 g) in water (18 ml) was added dropwise at 0° C. over 20 minutes to a stirred mixture of p-nitrophenylalanine (6.3 g, Fluka) c.HCl (3.1 ml), 5% aqu. H$_2$SO$_4$ (80 ml) and water (10 ml). When addition was complete, the mixture was stirred at 0° C. for 1 hour, then allowed to warm to room temperature over 2 hours. The mixture was extracted with ethyl acetate ($\times$4) and the extracts dried over MgSO$_4$ and evaporated in vacuo to give the desired product as a white solid (3.1 g).

(b) Methyl 2-hydroxy-3-(4-nitrophenyl)propionate

A solution of the product from step (a) (3.0 g) and c.HCl (0.5 ml) in methanol (100 ml) was refluxed for 1 hour. The solvents were evaporated in vacuo and the residue flash chromatographed through a silica column using methanol/chloroform (3:100 v/v) to give the desired product as a pale yellow solid (2.7 g). The 200 MHz $^1$H NMR was consistent with the proposed structure.

(c) 3-Benzyl-5-(4-nitrobenzyl)oxazolidin-2,4-dione

Benzyl isocyanate (1.2 g, Aldrich) was added at room temperature to a stirred solution of the product from step (b) (2.03 g) in toluene (25 ml). When addition was complete, the mixture was refluxed for 40 hours. The toluene was evaporated in vacuo and the residue flash chromatographed through a silica column using chloroform to give the desired product as a colourless oil which crystallised on standing (2.9 g). The product was recrystallised from IPA as fine white needles (1.8 g), mp 92°-93° C. The 200 MHz $^1$H NMR was consistent with the proposed structure.

SYNTHETIC EXAMPLE 6

Preparation of 1-Benzyl-4-(4-nitrobenzyl)imidazolidin-2,5-dione

Benzyl isocyanate (3.2 g, Aldrich) was added dropwise at 0° C. over 20 minutes to a stirred mixture of p-nitrophenylalanine (4.2 g, Fluka) and KOH (1.3 g) in water (40 ml). When addition was complete, the mixture was stirred at 60°-70° C. for 2 hours, then cooled, filtered, and the filtrate treated with c.HCl. The resulting white solid was filtered off, washed with ice-water, dried in vacuo, then suspended in 50% aqu. HCl (20 ml) and refluxed for 2 hours. The suspension was cooled, diluted with water, filtered, and the residue dried in vacuo to give the desired product (5.7 g).

SYNTHETIC EXAMPLE 7

Preparation of 5-Benzyl-3-[2-(4-nitrophenyl)ethyl]imidazolidin-2,4-dione (a) 5-Benzylimidazolidin-2,4-dione A solution of DL-$\beta$-phenylalanine (4.9 g, Aldrich) and potassium cyanate (2.4 g) in water (9 ml) was refluxed for 1 hour. C.HCl (4.5 ml) was added and the mixture refluxed for a further 10 minutes, then cooled, diluted with water, and the resulting precipitate filtered off, washed with ice-water, and dried in vacuo to give the desired product as a crystalline white solid (4.0 g).

(b) 5-Benzyl-3-[2-(4-nitrophenyl)ethyl]imidazolidin-2,4-dione

A solution of the product from step (a) (4.0 g) in DMF (10 ml) was added under $N_2$ to a stirred suspension of anhy. $K_2CO_3$ (3.0 g) in DMF (10 ml), followed by the addition of a solution of p-nitrophenethyl bromide (4.9 g, Aldrich) in DMF (5 ml). After additions were complete, the mixture was stirred at room temperature for 17 hours, then at 40° C. for 48 hours. The mixture was poured into ice-water, stirred for 2 hours, and the resulting precipitate filtered off, washed with water, and triturated with ethanol to give the desired product as a pale yellow solid (3.7 g).

SYNTHETIC EXAMPLE 8

Preparation of 3-Benzyl-1-(4-nitrobenzyl)imidazolidin-2,4-dione

A solution of 3-benzylimidazolidin-2,4-dione (5.7 g, JACS 1965, 3414) in DMF (10 ml) was added under $N_2$ to a stirred suspension of anhy. $K_2CO_3$ (4.1 g) in DMF (10 ml), followed by the addition of a solution of p-nitrobenzyl bromide (6.45 g, Aldrich) in DMF (10 ml). After additions were complete, the mixture was stirred at room temperature for 72 hours, then poured into ice-water and extracted with ethyl acetate ($\times$3). The combined extracts were washed with water ($\times$2) and brine, dried over $MgSO_4$ and evaporated to give a yellow oil which was flash chromatographed through a silica column using chloroform to give the desired product as a pale yellow solid (7.9 g).

SYNTHETIC EXAMPLE 9

Preparation of 4-Benzyl-1-(4-nitrobenzyl)-1,2,4-triazolidin-3,5-dione

A mixture of 4-benzylurazole (3.8 g, JCS Perkin II, 1975, 1325), p-nitrobenzyl bromide (4.3 g, Aldrich) and polymer-supported 1,5,7-triazabicyclo[4.4.0]dec-5-ene (P-TBD, 6.3 g, Fluka) in DCM (400 ml) was refluxed under $N_2$ for 24 hours. The P-TBD was filtered off and the filtrate evaporated to leave a gum which was flash chromatographed through a silica column using chloroform/methanol (19:1 v/v) to give the desired product as a solid (3.8 g).

SYNTHETIC EXAMPLE 10

Preparation of 3-Benzyl-1-(4-nitrobenzyl)pyrrolidin-2,5-dione (a) Triethyl 3-phenylpropane-1.2.2-tricarboxylate Sodium (2.3 g) was dissolved in dry ethanol (140 ml), triethylethane-1,1,2-tricarboxylate (24.8 g, Aldrich) and benzyl chloride were (12.8 g) added, and the mixture was stirred under reflux for 18 hours, then filtered and evaporated in vacuo. Water (100 ml) was added to the residue and extracted with ether ($\times$3). The combined extracts were washed with water, dried over $MgSO_4$ and evaporated in vacuo to give the desired product as a light yellow oil (32.6 g).

(b) Diethyl 3-phenylpropane-1,2-dicarboxylate

A solution of the product from step (a) (23.6 g) in c.HCl (326 ml) was stirred under reflux for 46 hours, then cooled. The resulting precipitate was extracted with chloroform ($\times$3) and the extracts combined, washed with 2M aqu. KOH ($\times$2), acidified to pH 4.0 (2M aqu. HCl) and cooled. The resulting precipitate was filtered off, washed with water and dried in vacuo to give the desired product (15.7 g). The 200 MHz $^1$H NMR was consistent with the proposed structure.

(c) 3-Benzylsuccinic anhydride

The product from step (b) was suspended in acetyl chloride (24 ml) and the suspension refluxed for 3 hours, then evaporated in vacuo to give a white solid which was triturated and washed with 60-80 petrol and dried in vacuo to give the desired product (9.7 g). The 200 MHz $^1$H NMR was consistent with the proposed structure.

(d) 3-Benzyl-1-(4-nitrobenzyl)pyrrolidin-2,5-dione

A suspension of p-nitrobenzylamine hydrochloride (8.1 g, Aldrich), and triethylamine (4.3 g) in DCM (40 ml) was added dropwise to a stirred solution of the product from step (c) (7.6 g) in DCM (40 ml) and the mixture stirred at room temperature for 3 hours, then evaporated in vacuo to give a foam to which benzene (82 ml) and acetyl chloride (20.5 ml) were added. The mixture was stirred for 20 minutes at room temperature, then refluxed for 5 hours and evaporated in vacuo. The residue was taken up in DCM (400 ml), washed with water ($\times$3), dried over $MgSO_4$ and evaporated in vacuo. The residue was triturated with petrol and dried in vacuo to give the desired product (12.7 g). The 200 MHz $^1$H NMR was consistent with the proposed structure.

SYNTHETIC EXAMPLE 11

Preparation of (−)-2-[5-{2,5-Dioxo-1-(3-phenoxybenzyl)imidazolidin-4-yl]methyl}-1H-indol-3-yl]ethylamine maleate hydrate (a) 3-Phenoxybenzamide Triethylamine (5.6 g) was added at 0° C. under $N_2$ to a stirred solution of 3-phenoxybenzoic acid (10.7 g, Aldrich) in THF (75 ml), followed by the addition of methyl chloroformate (4.7 g) at less than 5° C. After additions were complete, the mixture was stirred at 0° C. for 30 minutes. 0.88 Ammonia (30 ml) was added and the mixture stirred at room temperature for 20 hours, then evaporated in vacuo and the residue taken up in ethyl acetate (100 ml) and water (100 ml). The aqueous phase was separated, extracted with ethyl acetate and the combined ethyl acetate solutions washed with 5% w/v aqu. $Na_2CO_3$ (2$\times$50 ml), 2N aqu. HCl (50 ml) and water (100 ml), dried over $Na_2SO_4$ and evaporated in vacuo to give the desired product as a colourless solid which was recrystallised from ethyl acetate/60-80 pet. ether (1:2 v/v), mp 125°-127° C. (6.5 g). The 200 MHz $^1$H NMR was consistent with the proposed structure.

(b) 3-Phenoxybenzylamine

A solution of the product from step (a) (6.5 g) in THF (75 ml) was added under $N_2$ over 15 minutes to a stirred suspension of LAH (2.3 g) in THF (100 ml). After addition was complete, the mixture was refluxed for 5.5 hours, then cooled to $-5°$ C., excess LAH destroyed by the careful addition of 15% w/v aqu. NaOH (100 ml), and the mixture taken up in water (150 ml) and ether (200 ml). The aqueous phase was separated, extracted with ether and the combined ether solutions washed with 2N aqu. NaOH ($2 \times 100$ ml) and water ($2 \times 200$ ml), dried over $Na_2SO_4$ and evaporated in vacuo to give the desired product as a colourless oil (5.9 g). The 200 MHz $^1$H NMR was consistent with the proposed structure.

(c) (+)-Methyl 2-amino-3-(4-nitrophenyl)propionate hydrochloride

A solution of p-nitro-L-phenylalanine (12.6 g) and c.HCl (7.5 g) in methanol (150 ml) was refluxed for 1.5 hours and the solvent then evaporated in vacuo. The residue was triturated with ether and recrystallised from SVM to give the desired product as a off-white solid, $[\alpha]^{25}$ $+15.3°$ (c=0.55, MeOH).

(d) (+)-Methyl 2-isocyanato-3-(4-nitrophenyl)propionate

Phosgene was bubbled slowly into a refluxing suspension of the product from step (a) (5.0 g) in toluene (75 ml) for 6 hours. The mixture was cooled, filtered and the residue washed with toluene. The combined filtrate and washings were evaporated in vacuo to give the desired product as a white solid (2.0 g).

(e) (+)-1-[1-Methoxycarbonyl-2-(4-nitrophenyl)ethyl]-3-(3-phenoxybenzyl)urea A solution of the product from step (b) (1.6 g) in DCM (1 ml) was added at 0° C. under $N_2$ to a stirred solution of the product from step (d) (2.0 g) in DCM (20 ml). After addition was complete, the mixture was allowed to warm to room temperature over 1 hour with stirring. The mixture was evaporated in vacuo and the residue flash chromatographed through a silica column using methanol/chloroform (2:100 v/v) to give the desired product as a pale yellow solid which was recrystallised from DCM/ether (1:2 v/v). Mp 112°–114° C., $[\alpha]_D^{25}$ $+2.6°$ (c=0.51, MeOH), elemental analysis in accordance with proposed structure.

(f) (−)-5-(4-Nitrobenzyl-3-(3-phenoxybenzyl)imidazolidin-2,4-dione

A suspension of the product from step (e) (2.0 g) in 5N aqu. HCl (70 ml) was heated at 100° C. for 1.5 hours. The resulting off-white precipitate was filtered off, washed with water, dried and recrystallised from ethanol to give the desired product as white needles (1.3 g), $[\alpha]_D^{25}$ $-16.0°$ (c=0.51, MeOH).

SYNTHETIC EXAMPLE 12

Compounds of formula (V) wherein Y is >NH may be converted to compounds of formula (V) wherein Y is >NR$^5$, where R$^5$ is as hereinbefore defined other than hydrogen.

By way of example, the compound of formula (V) obtained in Synthetic Example 6 may be N-methylated in the hydantoin ring by the following method.

Preparation of 1-Benzyl-3-methyl-4-(4-nitrobenzyl)imidazolidin-2,5-dione

Methyl iodide (3.5 g) was added dropwise under $N_2$ to a stirred mixture of the compound of formula (V) obtained in Synthetic Example 6 and anhy. $K_2CO_3$ (1.9 g) in DMF (20 ml). After addition was complete, the mixture was stirred at room temperature for 24 hours. Further methyl iodide (0.8 ml) was added and the mixture stirred for a further 24 hours, then poured into water and extracted with ethyl acetate ($\times 3$). The combined extracts were washed with water ($\times 2$) and brine, dried over $MgSO_4$ and evaporated to give a yellow oil which was flash chromatographed through a silica column using chloroform. The desired product was obtained as a white crystalline solid (3.0 g).

SYNTHETIC EXAMPLES 13

Compounds of formula (V) wherein Z and/or Z' is >C=O may be converted to compounds of formula (IV) wherein Z and/or Z' is >CH$_2$.

By way of example, the compounds of formula (V) obtained in Synthetic Examples 8 and 12 may be converted from imidazolidin-2,4-diones to imidazolidin-2-ones by the following methods.

Preparation of 1-(4-Aminobenzyl)-3-benzylimidazolidin-2-one hydrochloride

(a) 1-Benzyl-3-(4-nitrobenzyl)-4-imidazolin-2-one

A suspension of LAH (370 mg) in THF (35 ml) was added under $N_2$ over 1 hour to a stirred solution of the compound of formula (V) obtained in Synthetic Example 8 (3.2 g) in THF (35 ml). After addition was complete, the mixture was stirred at room temperature for 17 hours, then 2N aqu. HCl (6 ml) was added, followed by c.HCl (2 ml). The resulting organic phase was separated and washed with brine, dried over $MgSO_4$ and evaporated in vacuo to give the desired product as a yellow oil (3.0 g).

(b) 1-(4-Aminobenzyl)-3-benzylimidazolidin-2-one hydrochloride

A mixture of the product from step (a) (3.0 g), 10% Pd/C (750 mg) and 2N aqu. HCl (4.7 ml) in ethanol/water (55 ml, 3:2 v/v) was hydrogenated at room temperature and atmospheric pressure for 24 hours (uptake 1100 ml). The mixture was filtered through celite, the residue washed with hot water and the filtrate evaporated in vacuo to give the desired product as a yellow oil (2.9 g). The 200 MHz $^1$H NMR and MS were consistent with the proposed structure.

Preparation of 4-(4-Aminobenzyl)-1-benzyl-3-methylimidazolidin-2-one hydrochloride

(a) 1-Benzyl-3-methyl-4-(4-nitrobenzyl)imidazolin-2-one

A solution of glac. acetic acid (2.0 ml) in IPA (8.3 ml) was added dropwise over 25 minutes to a stirred suspension of the compound of formula (V) obtained in Synthetic Example 12 (2.3 g) and sodium borohydride (1.3 g) in IPA (22 ml). After addition was complete, the mixture was stirred at room temperature for 20 hours. More IPA (30 ml) was added and the mixture refluxed for 4 hours, then cooled and more sodium borohydride (1.3 g) added. A further solution of glac. acetic acid (2.0 ml) in IPA (8.3 ml) was added dropwise to the stirred mixture. After addition was complete, the mixture was refluxed for 4 hours, then poured into 2N aqu. HCl and the latter extracted with ether (×3). The combined extracts were washed with brine, dried over MgSO$_4$ and evaporated in vacuo to give the desired product as a yellow oil (2.2 g).

(b)
4-(4-Aminobenzyl)-1-benzyl-3-methylimidazolidin-2-one hydrochloride

A mixture of the product from step (a) (2.2 g), 10% Pd/C (400 mg) and 2N aqu. HCl (4.3 ml) in ethanol/water (27.8 ml, 3:5 v/v) was hydrogenated at room temperature and atmospheric pressure for 24 hours (uptake ca 200 ml). The mixture was filtered through celite, the residue washed with hot water and the filtrate evaporated in vacuo to give the desired product as a white solid (2.1 g).

SYNTHETIC EXAMPLES 14

The compounds of formula (V) obtained in Synthetic Examples 1 to 12 may be converted to compounds of formula (I) by (i) reduction to the corresponding aniline, (ii) conversion of the aniline to the corresponding hydrazine, and (iii) cyclisation of the hydrazine to a compound of formula (I) by the Fischer indole synthesis. The compounds of formula (IV) obtained in Synthetic Example 13 require only steps (ii) and (iii).

By way of example, the compounds of formula (V) obtained in Synthetic Examples 1 and 4 may be converted to compounds of formula (I) by the following methods.

Preparation of
(±)-2-{5-[1-(3-Methylaminocarbonylbenzyl)-2,5-dioxoimidazolidin-4-ylmethyl]-1H-indol-3-yl}ethylamine (a)
3-[4-(4-Aminobenzyl)-2,5-dioxoimidazolidinylmethyl]-N-methylbenzamide hydrochloride A mixture of the product from step (c) in Synthetic Example 1 (4.5 g), 10% Pd/C (250 mg) and 2N aqu. HCl (5.7 ml) in ethanol/water (75 ml, 3:2 v/v) was hydrogenated at room temperature and atmospheric pressure for 5 hours (uptake 1200 ml). The mixture was filtered through Hyflo, the residue washed with water and the filtrate evaporated in vacuo to give the desired product as a pale mustard-coloured solid (4.6 g).

(b)
3-[4-(4-Hydrazinabenzyl)-2,5-dioxomidazolidinylmethyl]-N-methylbenzamide hydrochloride A solution of sodium nitrite (0.80 g) in water (8 ml) was added dropwise at −10° C. over 15 minutes to a stirred suspension of the product from step (d) (4.5 g) in c.HCl (28 ml) and water (16 ml). After addition was complete, the mixture was stirred at 0° C. for 15 minutes, then added dropwise at −10° C. over 15 minutes to a stirred solution of tin(II) chloride dihydrate in c.HCl (23 ml). After addition was complete, the mixture was allowed to warm to room temperature over 1 hour. The resulting precipitate was filtered off at 0° C., washed with cold ether, and dried in vacuo to give the desired product as a white solid (4.6 g).

(c)
(±)-2-{5-[1-(3-Methylaminocarbonylbenzyl)-2,5-dioxoimidazolidin-4-ylmethyl]-1H-indol-3-yl}ethylamine A mixture of the product from step (e) (1.21 g) and 4-chlorobutanal dimethyl acetal (456 mg, JACS 1951, 1365) in ethanol/water (60 ml, 5:1 v/v) was refluxed for 2 hours, then evaporated in vacuo and the residue flash chromatographed through a silica column using DCM/ethanol/ammonia (20:8:1 v/v/v) to give the desired product as a pale cream coloured oil (275 mg).

Preparation of
(±)-2-[5-(1-Benzyl-2,5-dioxopyrrolidin-3-ylmethyl)-1H-indol-3-yl]ethylamine (a)' 3-(4-Aminobenzyl)-1-benzylpyrrolidin-2,5-dione hydrochloride A mixture of the product from step (a) of Synthetic Example 4 (5.0 g), tin(II) chloride dihydrate (17.4 g) and c.HCl (3 ml) in ethanol (100 ml) was refluxed under N$_2$ for 3.5 hours, then poured into satd. aqu. NaHCO$_3$ (400 ml) and the mixture saturated with NaCl, basified to pH 8 by the addition of more satd. aqu. NaHCO$_3$, and extracted with ethyl acetate (×3). The combined extracts were washed with water (×2) and brine (×2), dried over MgSO$_4$ and evaporated in vacuo. The residue was crystallised from ethyl acetate/60–80 petrol (1:2 v/v) and air dried to give the desired product (2.9 g).

(b)'
1-Benzyl-3-(4-hydrazinobenzyl)pyrrolidin-2,5-dione hydrochloride

By analogy with step (b).

(c)'
(±)-2-[5-(1-Benzyl-2,5-dioxopyrrolidin-3-ylmethyl)-1H-indol-3-yl]ethylamine By analogy with step (c).

SYNTHETIC EXAMPLES 15

Compounds of formula (I) wherein $R^3 = R^4 = H$ may be converted to corresponding compounds of formula (I) wherein $R^3$ and/or $R^4$ are as hereinbefore defined other than hydrogen.

By way of example, the compound of formula (I) obtained in Synthetic Example 14, step (c), may be N-alkylated and the compound of formula (I) derived from the compound of formula (V) obtained in Example 2 may be N,N-dialkylated by the following methods.

Preparation of
(±)-N-Methyl-2-{5-[1-(3-methylaminocarbonylbenzyl)-2,5-dioxoimidazolidin-4-ylmethyl]-1H-indol-3-yl}ethylamine (a)
N-Benzyl-2-{5-[1-(3-methylcarbamoylbenzyl)-2,5-dioxoimidazolidin-4-ylmethyl]-1H-indol-3-yl}ethylamine A mixture of the compound of formula (I) obtained in step (c) of Synthetic Example 14 (860 mg) and benzaldehyde (224 mg) in ethanol (9 ml) was stirred at room temperature for 30 hours. Sodium borohydride (80 mg) was added portionwise over 10 minutes and the mixture then stirred at room temperature for 1 hour. The solvent was evaporated in vacuo and the residue taken up in 2N aqu. HCl, basified with NaHCO$_3$, saturated with K$_2$CO$_3$, and extracted with ethyl acetate (×3). The combined extracts were dried over MgSO₄ and evaporated in vacuo to give a pale yellow foam which was flash chromatographed through a silica column using DCM/ethanol/ammonia (50:8:1 v/v/v) to give the desired product as a colourless oil (623 mg).

(b)
N-Benzyl-N-methyl-2-{5-[1-(3-methylcarbamoylbenzyl)-2,5-dioxoimidazolidin-4-ylmethyl]-1H-indol-3-yl}ethylamine Dimethyl sulphate (168 mg) was added dropwise under N₂ to a stirred mixture of the product from step (g) (646 mg) and anhy. K₃CO₃ (424 mg) in DMF (25 ml). After addition was complete, the mixture was stirred for 4 hours at room temperature, then poured into water and extracted with ethyl acetate (×7). The combined extracts were washed with water and brine, dried over MgSO₄ and evaporated in vacuo to give a yellow oil which was flash chromatographed through a silica column using DCM/ethanol/ammonia (50:8:1 v/v/v) to give the desired product (333 mg).

(c)
(±)-N-Methyl-2-{5-[1-(3-methylaminocarbonylbenzyl)-2,5-dioxoimidazolidin-4-ylmethyl]-1H-indol-3-yl}ethylamine A mixture of the product from step (b) (257 mg) and 10% Pd/C (110 mg) in ethanol (16 ml) was hydrogenated at room temperature and atmospheric pressure for 6 hours (uptake 12 ml). The mixture was filtered through celite, the residue washed with ethanol and the filtrate evaporated in vacuo to give a colourless oil which was flash chromatographed through a silica column using DCM/ethanol/ammonia (50:8:1 v/v/v) to give the desired product as a colourless oil (87 mg).

Preparation of
(−)-N,N-Dimethyl-2-[5-{1-[2-(4-acetylaminophenyl)ethyl]-2,5-dioxoimidazolidin-4-ylmethyl}-1H-indol-3-yl]ethylamine A solution of formaldehyde (24 mg) in methanol (3.6 ml) was added dropwise under N₂ to a stirred mixture of the compound of formula (I) derived from the compound of formula (V) obtained in Synthetic Example 2 (171 mg), sodium cyanoborohydride (30 mg) and glac. acetic acid (120 mg) in methanol (3.6 ml). After addition was complete, the mixture was stirred for 2.5 hours, then satd. aqu. K₂CO₃ was added and the mixture extracted with ethyl acetate (×3). The combined extracts were washed with brine, dried over MgSO₄ and evaporated to give a white foam which was flash chromatographed through a silica column using DCM/ethanol/ammonia (30:8:1 v/v/v) to give the desired product as a colourless oil (155 mg).

SYNTHETIC EXAMPLE 16

Compounds of formula (I) may be converted to corresponding salts by treatment with the appropriate acids.

By way of example, the compound of formula (I) derived from the compound of formula (V) obtained in Synthetic Example 4 may be converted to the maleate salt by the following method.

Preparation of
(±)-2-[5-(1-Benzyl-2,5-dioxopyrrolidin-3-ylmethyl)-1H-indol-3-yl]ethylamine maleate dihydrate A solution of maleic acid (19 mg) and the compound of formula (I) derived from the compound of formula (V) obtained in Synthetic Example 4 (58.5 mg) in methanol (3 ml) was stood for 2.5 hours, evaporated in vacuo and the resulting solid freeze-dried from water to give the desired product (44 mg).

SYNTHETIC EXAMPLES 17 TO 28

By steps analogous to those described in Synthetic Examples 13 to 16, the compounds of formula (V) obtained in Synthetic Examples 1 to 12 were converted to the following compounds of formula (I). The 200 MHz ¹H NMR, MS and elemental analysis for each compound were consistent with the proposed structure.

17) (±)-2-{5-[1-(3-Methylaminocarbonylbenzyl)-2,5-dioxoimidazolidin-4-ylmethyl)-1H-indol-3-yl}ethylamine. 1.5 maleate. 0.5 ethyl acetate, mp 89°–94° C.;

18) (−)-N,N-Dimethyl-2-[5-{1-[2-(4-acetylaminophenyl)ethyl]-2,5-dioxoimidazolidin-4-ylmethyl}-1H-indol-3-yl]ethylamine maleate hydrate, mp 71° C. (softens 56°), $[\alpha]_D^{25}$ −18.3° (c=0.51, MeOH);

19) (±)-2-[5-(1-Benzyl-2,5-dioxopyrrolidin-3-ylmethyl)-1H-indol-3-yl]ethylamine maleate dihydrate;

20) (±)-2-{5-[(3-Benzyl-2,4-dioxooxazolidin-5-yl)methyl]-1H-indol-3-yl}ethylamine maleate hydrate;

21) (±)-2-[5-(1-Benzyl-3-methyl-2-oxoimidazolidin-4-ylmethyl)-1H-indol-3-yl]ethylamine. 1.2 maleate. 0.8 hydrate;

22) (±)-5-[5-Benzyl-2,4-dioxoimidazolidin-3-ylmethyl]-1H-indol-3-ylethylamine maleate hydrate, mp 88°–90° C.;

23) 2-[5-(3-Benzyl-2,4-dioxoimidazolidin-1-ylmethyl)-1H-indol-3-yl]ethylamine maleate hydrate. 0.5 ethanolate;

24) 2-[5-(4-Benzyl-3,5-dioxo-1,2,4-triazol-2-ylmethyl)-1H-indol-3-yl]ethylamine maleate hydrate;

25) (±)-2-[5-(3-Benzyl-2,5-dioxopyrrolidinylmethyl)-1H-indol-3-yl]ethylamine. 1.1 maleate. 1.3 hydrate;

26) (−)-2-[5-{[2,5-Dioxo-1-(3-phenoxybenzyl))imidazolidin-4-yl]methyl}-1H-indol-3-yl]ethylamine maleate hydrate, $[\alpha]_D^{25}$ −11.4° (c=0.52, MeOH);

27) (±)-N-Methyl-2-{5-[1-(3-methylaminocarbonylbenzyl)-2,5-dioxoimidazolidin-4-ylmethyl]-1H-indol-3-yl}ethylamine maleate hydrate;

28) (−)-N,N-Dimethyl-2-{5-[2,5-dioxo-1-(3-phenoxybenzyl)imidazolidin-4-ylmethyl]-1H-indol-3-yl}ethylamine maleate. 1.5 hydrate, $[\alpha]_D^{25}$ −7.2° (c=0.56, MeOH);

SYNTHETIC EXAMPLES 29 TO 91

By steps analogous to those described in Synthetic Examples 1 to 16, the following compounds of formula (I) were prepared. The 200 MHz ¹H NMR, MS and elemental analysis for each compound were consistent with the proposed structure.

29) (±)-2-[5-(1-Benzyl-2,5-dioxoimidazolidin-4-yl)-1H-indol-3-yl]ethylamine hydrochloride, mp 233°–240° C. (dec. 173°–174° C.);

30) (±)-2-{5-[2,4-Dioxo-3-(2-phenylethyl)imidazolidin-5-ylmethyl]-1H-indol-3-yl}ethylamine maleate. 0.5 hydrate, mp 98°–100° C.;

31) (±)-2-{5-[1-(4-Biphenylylmethyl)-2,5-dioxoimidazolidin-4-ylmethyl]-1H-indol-3-yl}ethylamine maleate. 1.5 hydrate, mp 132°–134° C. (softens 115° C.);

32) (±)-2-[5-(4-Benzyl-2,5-dioxoimidazolidin-1-yl)-1H-indol-3-yl]ethylamine maleate hydrate, mp 130°–135° C.;

33) (±)-N,N-Dimethyl-2-[5-(1-phenylethyl-2,5-dioxoimidazolidin-4-ylmethyl)-1H-indol-3-yl]ethylamine maleate. 1.5 hydrate, mp 65°–70° C.;

34) (±)-2-[5-(3-Thienyl-2,4-dioxoimidazolidin-5-ylmethyl)-1H-indol-3-yl]ethylamine maleate;

35) (±)-3-[3-(2-Aminoethyl)-1H-indol-5-ylmethyl]-5-benzylimidazolidin-2,4-dione maleate. 1.3 hydrate, mp 111°–113° C. (softens 86° C.);

36) (±)-2-[5-{[2,5-Dioxo-1-(3-phenoxybenzyl)imidazolidin-4-yl]methyl}-1H-indol-3-yl]ethylamine maleate dihydrate, softens 75° C.;

37) (±)-2-{5-[(1,3-Dibenzyl-2,5-dioxoimidazolidin-4-yl)methyl]-1H-indol-3-yl}ethylamine. 1.5 maleate. 1.5 hydrate;

38) (±)-2-[5-(3-Benzyl-1-methyl-2,5-dioxoimidazolidin-4-ylmethyl)-1H-indol-3-yl]ethylamine maleate. 0.5 hydrate;

39) (±)-2-{5-[2,5-Dioxo-1-(3-phenylpropyl)imidazolidin-4-ylmethyl]-1H-indol-3-yl}ethylamine maleate. 0.8 hydrate;

40) (±)-2-{5-[2-(1-Benzyl-2,5-dioxoimidazolidin-4-yl)ethyl]-1H-indol-3-yl}ethylamine maleate. 0.8 hydrate, mp 139° C.;

41) (±)-N,N-Dimethyl-2-{5-[2,5-dioxo-1-(3-phenoxybenzyl)imidazolidin-4-ylmethyl]-1H-indol-3-yl}ethylamine maleate hydrate;

42) (±)-2-[5-(1-Benzyl-3-methyl-2,5-dioxoimidazolidin-4-ylmethyl)-1H-indol-3-yl]ethylamine maleate hydrate;

43) (±)-2-[5-{[2,5-Dioxo-1-(4-phenylsulphonybenzyl)imidazolidin-4-yl]methyl}-1H-indol-3-yl]ethylamine maleate. 1.3 hydrate, softens 80° C. (dec. 153°–155° C.);

44) (±)-2-[5-}[2,5-Dioxo-1-(3-phenylsulphonybenzyl)imidazolidin-4-yl]methyl}-1H-indol-3-yl]ethylamine maleate. 1.3 hydrate, mp 137°–139° C. (softens 118° C.);

45) (±)-2-[5-{2,5-Dioxo-1-[3-(9-oxafluorene)methyl]imidazolidin-4-yl}methyl-1H-indol-3-yl]ethylamine maleate. 1.3 hydrate, dec. 124° C.;

46) (±)-N-{4-[5-(3-(2-Aminoethyl)-1H-indol-5-yl)-2,5-dioxoimidazolidin-4-ylmethyl]methyl}phenylacetamide maleate hydrate, dec. 163°–165° C.;

47) (±)-2-[5-{[1-(3-Benzamidobenzyl)-2,5-dioxoimidazolidin-4-yl]methyl}-1H-indol-3-yl]ethylamine maleate dihydrate, softens 142° C. (dec. 175°–177° C.);

48) (±)-2-[5-{[1-(4-Anilinocarbonylbenzyl)-2,5-dioxoimidazolidin-4-yl]methyl}-1H-indol-3-yl]ethylamine maleate. 1.8 hydrate, softens 122°–124° C. (dec. 168°–172° C.);

49) (±)-2-[5-{2-[2,5-Dioxo-1-(thien-2-ylmethyl)imidazolidin-4-yl]ethyl}-1H-indol-3-yl]ethylamine. 1.2 maleate hydrate, mp 145°–146° C. (softens 140° C.);

50) (±)-2-{5-[1-(4-Methoxybenzyl)-2,5-dioxoimidazolidin-4-ylmethyl]-1H-indol-3-yl}ethylamine maleate. 1.3 hydrate, mp 149°–151° C. (softens 100° C.);

51) (±)-N,N-Dimethyl-2-{5-[2-(2,5-Dioxo-1-thienylmethylimidazolidin-4-yl)ethyl]-1H-indol-3-yl}ethylamine maleate hydrate;

52) (±)-N,N-Di-n-propyl-2-{5-[2-(2,5-Dioxo-1-thienylmethylimidazolidin-4-yl)ethyl]-1H-indol-3-yl}ethylamine maleate hydrate, softens 60° C. (dec. 81°–83° C.);

53) (±)-2-{5-[1-(4-Chlorobenzyl)-2,5-dioxoimidazolidin-4-ylmethyl]-1H-indol-3-yl}ethylamine maleate hydrate, softens 104° C. (dec. 130° C.);

54) (±)-2-{4-[3-(2-Aminoethyl)-1H-indol-5-ylmethyl]-2,5-dioxoimidazolidin-1-ylmethyl}-N-methylbenzamide maleate dihydrate;

55) (±)-3-[3-(2-Aminoethyl)-1H-indol-5-ylmethyl]-5-thienylimidazolidin-2,4-dione maleate, dec. 194°–196° C.;

56) (±)-N-{3-[4-{[3-(2-Dimethylaminoethyl)-1H-indol-5-yl]methyl}-2,5-dioxoimidazolidin-1-ylmethyl]phenyl}benzamide maleate ethanolate hydrate, dec. 116°–122° C.;

57) (±)-N,N-Dimethyl-2-[5-{[2,5-dioxo-1-(thien-2-ylmethyl)imidazolidin-4-yl]methyl}-1H-indol-3-yl]ethylamine maleate, mp 114°–116° C. (softens 80° C.);

58) (±)-2-[5-{[2,5-Dioxo-1-(3-phenylaminocarboxybenzyl)imidazolidin-4-yl]methyl}-1H-indol-3-ylethylamine. 1.3 maleate. 1.3 hydrate, softens 102° C. (dec. 162° C.);

59) (±)-N,N-Dimethyl-2-{5-[2-(1-benzyl-2,5-dioxoimidazolidin-4-yl)ethyl]-1H-indol-3-yl}ethylamine maleate. 0.5 hydrate, mp 79°–82° C.;

60) (±)-N,N-Dimethyl-2-{5-[1-(3-methylcarbonylaminophenylmethyl)-2,5-dioxoimidazolidin-4-ylmethyl]-1H-indol-3-ylmethyl}ethylamine maleate. 1.5 hydrate, mp 128°–130° C.;

61) (±)-2-{5-[1-(3-Acetylaminobenzyl)-2,5-dioxoimidazolidin-4-ylmethyl]-1H-indol-3-yl}ethylamine. 1.5 maleate hydrate, softens 96° C. (dec. 135° C.);

62) (±)-2-{5-[1-(2-Acetylaminobenzyl)-2,5-dioxoimidazolidin-4-ylmethyl]-1H-indol-3-yl}ethylamine. 1.5 maleate hydrate, softens 75° C.;

63) (±)-2-{5-[1-(3-Isopropylaminocarbonylbenzyl)-2,5-dioxoimidazolin-4-ylmethyl]-1H-indol-3-yl}ethylamine maleate hydrate, mp 120°–125° C. (dec. 146°–150° C.);

64) (±)-2-{5-[3-Methyl-2,5-dioxo-4-(2-thienyl)imidazolidin-1-ylmethyl]-1H-indol-3-ylmethyl]-1H-indol-3-yl}ethylamine maleate. 0.8 hydrate, softens 90°–95° C. (dec. 180°–182° C.);

65) (±)-2-[5-{[2,5-Dioxo-1-(xanthen-3-yl)imidazolidin-4-yl]methyl}-1H-indol-3-yl]ethylamine maleate hydrate, dec. 147° C.;

66) (±)-N,N-Dimethyl-2-{5-[1-(3-methylaminocarboxybenzyl)-2,5-dioxoimidazolidin-4-ylmethyl]-1H-indol-3-yl}ethylamine maleate hydrate;

67) (±)-N,N-Dimethyl-2-{5-[3-(3-anilinocarbonylbenzyl)-2,4-dioxoimidazolidin-5-ylmethyl]-1H-indol-3-yl}ethylamine maleate dihydrate, mp 120°–125° C.;

68) (±)-2-[5-{1-[3-(4-Chlorophenylcarbamoyl)benzyl]-2,5-dioxoimidazolidin-4-ylmethyl}-1H-indol-3-yl]ethylamine maleate dihydrate, mp 144° C.;

69) (±)-2-{5-[1-(3-Methylsulphaminobenzyl)-2,5-dioxoimidazolidin-4-ylmethyl]-1H-indol-3-yl}ethylamine maleate. 0.8 hydrate, mp 122° C. (softens 104° C.);

70) (±)-2-{5-[2,5-Dioxo-1-(2-thien-2-ylethyl)imidazolidin-4-ylmethyl]-1H-indol-3-yl}ethylamine maleate. 1.5 hydrate, dec. 62° C.;

71) (±)-2-[5-{1-[2-(4-Methoxyphenyl)ethyl]-2,5-dioxoimidazolidin-4-ylmethyl}-1H-indol-3-yl]ethylamine maleate;

72) (±)-2-[5-{1-[3-(4-Methoxyphenylaminocarbonyl)benzyl-2,5-dioxoimidazolidin-4-ylmethyl}-1H-indol-3-yl]ethylamine maleate. 1.5 hydrate, softens 111° C. (dec. 135°–136° C.);

73) (±)-2-[5-{2-[2-(4-Acetylaminophenyl)ethyl]-2,5-dioxoimidazolidin-4-ylmethyl}-1H-indol-3-yl]ethylamine maleate hydrate, mp 126°–127° C.;

74) (±)-N,N-Dimethyl-2-{5-[2-(5-Benzyl-2,4-dioxoimidazolidin-3-yl)ethyl]-1H-indol-3-yl}ethylamine maleate. 0.3 hydrate, mp 70°–71° C.;

75) (±)-2-{5-[1-(2-N,N-Dimethylcarbamoylbenzyl)-2,5-dioxoimidazolidin-4-ylmethyl]-1H-indol-3-yl}ethylamine maleate. 1.3 hydrate, mp 119°–121° C. (softens 93° C.);

76) (±)-2-[5-{2-[1-(3-Acetamidobenzyl)-2,5-dioxoimidazolidin-4-yl]ethyl-1H-indol-3-yl]ethylamine 1.4 maleate. 0.8 hydrate;

77) (±)-N,N-Dimethyl-2-[5-{2-[1-(3-acetamidobenzyl)-2,5-dioxoimidazolidin-4-yl]ethyl}ethylamine. 1.6 maleate. 1.8 hydrate;

78) (±)-2-{5-[(3-(N-Ethylcarbamoyl)benzyl)-2,5-dioxoimidazolidin-4-ylmethyl]-1H-indol-3-yl}ethylamine. 1.5 maleate hydrate, mp 55° C. (softens 35° C.);

79) (±)-N-Benzyl-N-methyl-2-{5-[1-(3-methylaminocarbonylbenzyl)-2,5-dioxoimidazolidin-4-ylmethyl]-1H-indol-3-yl}ethylamine maleate dihydrate;

80) (±)-2-[5-{2-[1-(4-Acetamidobenzyl)-2,5-dioxomidazolidin-4-yl)ethyl}-H-indol-3-yl]ethylamine. 1.4 maleate. 1.3 hydrate;

81) (±)-2-{5-[1-(4-Cyanobenzyl)-2,5-dioxoimidazolidin-4-ylmethyl]-1H-indol-3-yl}ethylamine maleate hydrate;

82) (±)-N,N-Dimethyl-2-{5-[1-(4-Cyanobenzyl)-2,5-dioxoimidazolidin-4-ylmethyl]-1H-indol-3-yl}ethylamine maleate. 1.5 hydrate;

83) (±)-N,N-Diethyl-2-[5-{1-[2-(4-Acetamidophenyl)ethyl]-2,5-dioxoimidazolidin-4-ylmethyl}-1H-indol-3-yl]ethylamine maleate hydrate;

84) (±)-N-Benzyl-N-methyl-2-[5-{1-[2-acetamidophenyl)ethyl]-2,5-dioxoimidazolidin-4-ylmethyl}-1H-indol-3-yl]ethylamine maleate hydrate;

85) (±)-N-Methyl-2-[5-{1-[2-(4-acetamidophenyl)ethyl]-2,5-dioxoimidazolidin-4-ylmethyl}-1H-indol-3-yl]ethylamine maleate hydrate;

86) (±)-2-{5-[4-(3-Methoxybenzyl)-2,5-dioxoimidazolidinylmethyl]-1H-indol-3-yl}ethylamine maleate hydrate;

87) (±)-2-{5-[4-(4-Methoxybenzyl)-2,5-dioxoimidazolidinylmethyl]-1H-indol-3-yl}ethylamine maleate hydrate;

88) 2-[5-(3-Benzyl-2,5-dioxoimidazolidinylmethyl)-1H-indol-3-yl]ethylamine maleate. 0.5 hydrate, softens 91° C. (dec. 149°–151° C.);

89) 2-[5-(3-Benzyl-2-oxoimidazolidinylmethyl)-1H-indol-3-yl]ethylamine maleate.

PHARMACEUTICAL FORMULATION EXAMPLES

In the following Examples, the active compound may be any compound of formula (I) and/or a physiologically acceptable salt or solvate thereof.

(i) Tablet Formulations

The following formulations A and B may be prepared by wet granulation of ingredients (a) to (c) and (a) to (d) with a solution of povidone, followed by addition of the magnesium stearate and compression.

|  |  | mg/tablet | mg/tablet |
|---|---|---|---|
| Formulation A | | | |
| (a) | Active ingredient | 250 | 250 |
| (b) | Lactose B.P. | 210 | 26 |
| (c) | Sodium Starch Glycollate | 20 | 12 |
| (d) | Povidone B.P. | 15 | 9 |
| (e) | Magnesium Stearate | 5 | 3 |
| | | 500 | 300 |
| Formulation B | | | |
| (a) | Active ingredient | 250 | 250 |
| (b) | Lactose 150 | 150 | — |
| (c) | Avicel PH 101 | 60 | 26 |
| (d) | Sodium Starch Glycollate | 20 | 12 |
| (e) | Povidone B.P. | 15 | 9 |
| (f) | Magnesium Stearate | 5 | 3 |
| | | 500 | 300 |
| Formulation C | | | |
| Active ingredient | | 100 | |
| Lactose | | 200 | |
| Starch | | 50 | |
| Povidone | | 5 | |
| Magnesium Stearate | | 4 | |
| | | 359 | |

The following formulations D and E may be prepared by direct compression of the admixed ingredients. The lactose used in formulation E is of the direct compression type.

|  | mg/capsule |
|---|---|
| Formulation D | |
| Active ingredient | 250 |
| Magnesium Stearate | 4 |
| Pregelatinised Starch NF15 | 146 |
| | 400 |
| Formulation E | |
| Active ingredient | 250 |
| Magnesium Stearate | 5 |
| Lactose | 145 |
| Avicel | 100 |
| | 500 |

|  | mg/tablet |
|---|---|
| Formulation F (Controlled releae formulation) | |
| (a) Active ingredient | 500 |
| (b) Hydroxypropylmethylcellulose (Methocel K4M Premium) | 112 |
| (c) Lactose B.P. | 53 |
| (d) Povidone B.P.C. | 28 |
| (e) Magnesium Stearate | 7 |
| | 700 |

The formulation may be prepared by wet granulation of ingredients (a) to (c) with a solution of povidone, followed by addition of the magnesium stearate and compression.

(ii) Capsule Formulations

Formulation A

Capsules may be prepared by admixing the ingredients of Formulation D above and filling two-part hard gelatin capsules with the resulting mixture. Formulation B (infra) may be prepared in a similar manner.

|  | mg/capsule |
|---|---|
| Formulation B | |
| (a) Active ingredient | 250 |
| (b) Lactose B.P. | 143 |
| (c) Sodium Starch Glycollate | 25 |

|   |   | mg/capsule |
|---|---|---|
| (d) | Magnesium Stearate | 2 |
|   |   | 420 |

Formulation C

| (a) | Active ingredient | 250 |
|---|---|---|
| (b) | Macrogol 4000 BP | 350 |
|   |   | 600 |

Capsules may be prepared by melting the Macrogol 4000 BP, dispersing the active ingredient in the melt, and filling two-part hard gelatin capsules therewith.

| Formulation D | mg/capsule |
|---|---|
| Active ingredient | 250 |
| Lecithin | 100 |
| Arachis Oil | 100 |
|   | 450 |

Capsules may be prepared by dispersing the active ingredient in the lecithin and arachis oil and filling soft, elastic gelatin capsules with the dispersion.

| Formulation E (Controlled release capsule) |   | mg/capsule |
|---|---|---|
| (a) | Active ingredient | 250 |
| (b) | Microcrystalline Cellulose | 125 |
| (c) | Lactose BP | 125 |
| (d) | Ethyl Cellulose | 13 |
|   |   | 513 |

The controlled release capsule formulation may be prepared by extruding mixed ingredients (a) to (c) using an extruder, then spheronising and drying the extrudate. The dried pellets are coated with a release-controlling membrane (d) and filled into two-part, hard gelatin capsules.

(iii) Intravenous Injection Formulation

| Active ingredient | 0.200 g |
|---|---|
| Sterile, pyrogen-free phosphate buffer (pH 9.0) | to 10 ml |

The active ingredient is dissolved in most of the phosphate buffer at 35°–40° C., then made up to volume and filtered through a sterile micropore filter into sterile 10 ml glass vials (Type 1) which are sealed with sterile closures and overseals.

(iv) Intramuscular Injection Formulation

| Active ingredient |   | 0.20 g |
|---|---|---|
| Benzyl Alcohol |   | 0.10 g |
| Glycofurol 75 |   | 1.45 g |
| Water for Injection | q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml glass vials (Type 1).

(v) Syrup Formulation

| Active ingredient | 0.2500 g |
|---|---|
| Sorbitol Solution | 1.5000 g |
| Glycerol | 1.0000 g |
| Sodium Benzoate | 0.0050 g |
| Flavour | 0.0125 ml |
| Purified Water | q.s. to 5.0 ml |

The sodium benzoate is dissolved in a portion of the purified water and the sorbitol solution added. The active ingredient is added and dissolved. The resulting solution is mixed with the glycerol and then made up to the required volume with the purified water.

(vi) Suppository Formulation

|   | mg/suppository |
|---|---|
| Active ingredient (63 μm)* | 250 |
| Hard Fat, BP (Witepsol H15 - Dynamit NoBel) | 1770 |
|   | 2020 |

*The active ingredient is used as a powder wherein at least 90% of the particles are of 63 μm diameter or less.

One-fifth of the Witepsol H15 is melted in a steam-jacketed pan at 45° C. maximum. The active ingredient is sifted through a 200 μm sieve and added to the molten base with mixing, using a Silverson fitted with a cutting head, until a smooth dispersion is achieved. Maintaining the mixture at 45° C., the remaining Witepsol H15 is added to the suspension which is stirred to ensure a homogenous mix. The entire suspension is then passed through a 250 μm stainless steel screen and, with continuous stirring, allowed to cool to 40° C. At a temperature of 38°–40° C., 2.02 g aliquots of the mixture are filled into suitable plastic moulds and the suppositories allowed to cool to room temperature.

(vii) Pessary Formulation

|   | mg/pessary |
|---|---|
| Active ingredient (63 μm) | 250 |
| Androus Dextrose | 380 |
| Potato Starch | 363 |
| Magnesium Stearate | 7 |
|   | 1000 |

The above ingredients are mixed directly and pessaries prepared by compression of the resulting mixture.

BIOLOGICAL ASSAY

The compounds of formula (I) prepared in Synthetic Examples 1 to 16 were each tested for their activity as agonists for the "5-HT$_1$-like" receptor mediating smooth muscle contraction by the following method.

Right and left lateral saphenous veins were obtained from male New Zealand White rabbits (2.4–2.7 kg) which had been killed by intravenous injection of pentobarbitone sodium (60 mg/kg). Ring segments (3–5 mm wide) prepared from each vessel were suspended between two wire hooks and immeresed in 20 ml organ baths containing Krebs' solution (pH 7.4) of the following composition (mM): NaCl 118.41, NaHCO$_3$ 25.00, KCl 4.75, KH$_2$PO$_4$ 1.19, MgSO$_4$ 1.19, glucose 11.10 and CaCl$_2$ 2.50. Cocaine (30 μM) was present in the Krebs' solution throughout the experiment to prevent the uptake of amines by sympathetic neurones. The Krebs' solution was maintained at 37° C. and continually gassed with 95% oxygen/5% carbon dioxide. Increases in tissue isometric force were measured using Grass FT03C force displacement transducers and recorded on a Gould BD-212 pen recorder.

A force of 1.0 g was applied to each preparation and re-established twice during a subsequent period of 30 minutes. During this period, tissues were exposed to pargyline (500 μM) to irreversibly inhibit monoamine oxidase and to phenoxybenzamine (0.1 μM) to inactivate $\alpha_1$-adrenoceptors. At the end of the 30 minutes, the inhibitors were removed by several changes of the organ bath Krebs' solution.

Agonist activity was assessed by cumulative additions of the test compound, its concentration being increased in 0.5 $\log_{10}$ unit increments until further additions caused no further change in tissue force. In each experiment, the activity of the test compound was compared to the activity of 5-HT. Activity was expressed in terms of the $p[A_{50}]$ ($-\log_{10}[M]$, where M is the molar concentration of agonist required to produce half the maximum effect). The results obtained are shown in Table 1.

TABLE 1

| Example | Activity $p[A_{50}]$ |
|---|---|
| 17 | 6.31 |
| 18 | 6.22 |
| 19 | 6.55 |
| 20 | 5.96 |
| 21 | 7.53 |
| 22 | 7.29 |
| 23 | 5.81 |
| 24 | 4.39 |
| 25 | 5.39 |
| 26 | 7.44 |
| 27 | 6.31 |
| 28 | 6.65 |
| 29 | 6.14 |
| 30 | 6.67 |
| 31 | 6.70 |
| 32 | 4.59 |
| 33 | 6.02 |
| 34 | 6.41 |
| 35 | 5.92 |
| 36 | 7.44 |
| 37 | 5.20 |
| 38 | 6.06 |
| 39 | 6.56 |
| 40 | 6.62 |
| 41 | 6.65 |
| 42 | 6.01 |
| 43 | 6.64 |
| 44 | 6.89 |
| 45 | 6.39 |
| 46 | 5.81 |
| 47 | 7.26 |
| 48 | 5.91 |
| 49 | 6.56 |
| 50 | 6.46 |
| 51 | 6.50 |
| 52 | 5.31 |
| 53 | 7.00 |
| 54 | 5.47 |
| 55 | 5.58 |
| 56 | 6.28 |
| 57 | 5.20 |
| 58 | 6.62 |
| 59 | 6.26 |
| 60 | 5.71 |
| 61 | 6.26 |
| 62 | 5.63 |
| 63 | 6.81 |
| 64 | 4.84 |
| 65 | 6.72 |
| 66 | 6.04 |
| 67 | 6.33 |
| 68 | 6.72 |
| 69 | 6.65 |
| 70 | 6.57 |
| 71 | 6.90 |

TABLE 1-continued

| Example | Activity $p[A_{50}]$ |
|---|---|
| 72 | 6.43 |
| 73 | 69.5 |
| 74 | 6.83 |
| 75 | 6.51 |
| 76 | 6.45 |
| 77 | 6.50 |
| 78 | 6.31 |
| 79 | 5.81 |
| 80 | 5.93 |
| 81 | 5.63 |
| 82 | 5.19 |
| 83 | 5.50 |
| 84 | 5.30 |
| 85 | 6.24 |
| 86 | 5.55 |
| 87 | 6.03 |
| 88 | 5.28 |

We claim:

1. A compound of formula (I)

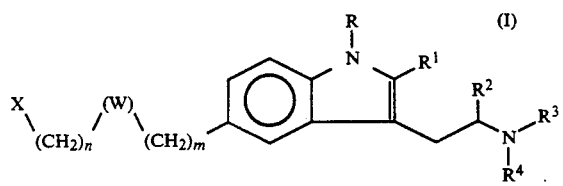

wherein

R, $R^1$ and $R^2$ are independently selected from hydrogen and $C_{1-4}$ alkyl;

$R^3$ and $R^4$ are independently selected from hydrogen, $C_{1-6}$ alkyl, $C_{3-6}$ cycloalkyl, aryl, and benzyl, wherein the alkyl, cycloalkyl, aryl or benzyl group is optionally substituted by one or more atoms or groups independently selected from halogen, $C_{1-4}$ alkyl and aryl, provided $R^3 \neq$ benzyl or substituted benzyl when $R^4 = H$;

m is an integer of from 0 to 2;

n is an integer of from 0 to 3;

(W) is a group of formula (i), (ii), (iii) or (iv)

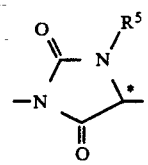

(i)

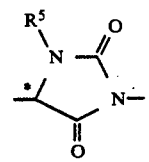

(ii)

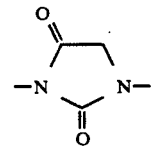

(iii)

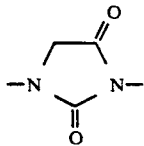 (iv)

wherein, in formulae (i) and (ii), $R^5$ is hydrogen, $C_{1-4}$ alkyl or benzyl, and the chiral center *in formula (i) or (ii) is in its (S) or (R) form or is mixture thereof in any proportions;

X is phenyl which group is optionally substituted by an atom or group selected from $C_{1-6}$ alkyl
$C_{3-6}$ cycloalkyl
phenyl
$C_{1-4}$ alkoxy
phenoxy
alkylsulphonyl
phenylsulphonyl
halogen
cyano
carbamoyl
alkylcarbamoyl
dialkylcarbamoyl
phenylcarbamoyl
diphenylcarbamoyl
carbamoylmethyl
N-alkylcarbamoylmethyl
N,N-dialkylcarbamoylmethyl
N-phenylcarbamoylmethyl
N,N-diphenylcarbamoylmethyl
alkoylamino
benzoylamino
alkoylaminomethyl
benzoylaminomethyl
alkylsulphamino
phenylsulphamino
alkylsulphaminomethyl
phenylsulphaminomethyl
sulphamyl
alkylsulphamyl
dialkylsulphamyl
phenylsulphamyl or
diphenylsulphamyl the phenyl group(s) of phenyl-containing substituents being optionally substituted by halogen or $C_{1-4}$ alkoxy;

or a salt or solvate thereof.

2. A compound of formula (I) as claimed in claim 1, or a salt or solvate thereof, in which (W) is (i) wherein $Y=O$, $CH_2$, or $NR^5$, $Z=CO$ or $CH_2$ and $Z'=CO$, (W) is (ii) wherein $Y=CH_2$ or $NR^5$ and $Z=Z'=CO$, (W) is (iii) wherein $Y=CH_2$ or $NR^5$, $Z=CO$ and $Z'=CO$ or $CH_2$, or (W) is (iv) wherein $Y=CH_2$, $Z=CO$ and $Z'=CO$ or $CH_2$, and X is a phenyl ring substituted by an alkylcarbamoyl, alkoylamino, or alkylsulphamino group.

3. A compound of formula (I) as claimed in claim 1 or 2, or a salt or solvate thereof, which compound is 2-{5-[1-(3-methylaminocarbonylbenzyl)-2,5-dioxoimidazolidin-4-ylmethyl]-1H-indol-3-yl}ethylamine, N,N-dimethyl-2-[5-{1-[2-(4-acetylaminophenyl)ethyl]-2,5-dioxoimidazolidin-4-ylmethyl}-1H-indol-3-yl]ethylamine, N-methyl-2-{5-[1-(3-methylaminocarbonylbenzyl)-2,5-dioxoimidazolidin-4-ylmethyl]-1H-indol-3-yl}ethylamine, 2-{-5-[1-(3-acetylaminobenzyl)-2,5-dioxoimidazolidin-4-ylmethyl]-1H-indol-3-yl}-ethylamine, and 2-{5-[1-(3-methylsulphonylaminobenzyl)-2,5-dioxoimidazolidin-4-ylmethyl]-1H-indol-3-yl}-ethylamine, or a salt or solvate of any thereof.

4. A method of treatment or prophylaxis of a clinical condition in a human or animal in which a selective agonist for the particular type of "5-HT-like" receptor as described herein is indicated which comprises the administration to said human or animal of a therapeutically effective amount of a compound of formula (I) as recited in claims 1 or 2, or a physiologically acceptable salt or solvate thereof.

5. A method according to claim 4 wherein the clinical condition is one in which vasoconstruction in the carotid vascular bed is indicated.

6. A method according to claim 4 wherein the clinical condition is migraine.

7. A pharmaceutical formulation comprising a compound of formula (I) as claimed according to any one of claims 1 through 3, or a physiologically acceptable salt or solvate thereof, and an acceptable carrier therefor.

8. (±)-5-[5-Benzyl-2,4-dioxoimidazolidin-3-ylmethyl]-1H-indol-3-yl]ethylamine maleate hydrate.

9. The compound of formula (I) as claimed in claim 1, or a salt or solvate thereof, wherein X is phenyl.

* * * * *